United States Patent [19]

Takasawa et al.

[11] Patent Number: 4,634,670
[45] Date of Patent: Jan. 6, 1987

[54] PROCESS FOR THE PREPARATION OF CELLULASE

[75] Inventors: Seigo Takasawa; Yasushi Morikawa, both of Kanagawa, Japan

[73] Assignee: Shin Nenryoyu Kaihatsu Gijutsu Kenkyu Kumiai, Toyko, Japan

[21] Appl. No.: 634,940

[22] Filed: Jul. 27, 1984

[30] Foreign Application Priority Data

Jul. 27, 1983 [JP] Japan ................................ 58-137256

[51] Int. Cl.⁴ ........................ C12N 9/42; C12N 15/00; C12N 1/14; C12R 1/885
[52] U.S. Cl. .................................. 435/209; 435/172.1; 435/254; 435/945
[58] Field of Search ........................ 435/209, 254, 945

[56] References Cited

U.S. PATENT DOCUMENTS 4,275,163 6/1981 Gallo .................................... 435/209
4,472,504 9/1984 Gallo .................................... 435/209

OTHER PUBLICATIONS

Tatum et al, Science, vol. 109, pp. 509-511, May 1949.

Primary Examiner—Lionel M. Shapiro
Attorney, Agent, or Firm—Wolder, Gross & Yavner

[57] ABSTRACT

Cellulase may be prepared in good yield and at relatively low cost by culturing certain mutant strains of the genus Trichoderma, which exhibit increased inducibility of cellulase by L-sorbose, in medium wherein the carbon source comprises cellulose-containing material of plant origin, for example, bagasses, waste papers, rice plant hulls and straws or soybean wastes. Preferred mutant strains are exemplified by *Trichoderma reesei* PC-1-4, PC-3-7, X-30 and X-31.

7 Claims, No Drawings

PROCESS FOR THE PREPARATION OF CELLULASE

BACKGROUND OF THE INVENTION

The present invention relates to a fermentation process for the preparation of cellulase. By this process, a good yield of cellulase at relatively low cost may be obtained, using cellulose-containing waste materials resulting from agricultural and forest industries as the carbon source.

The term "cellulase" used in this specification denotes both β-glucanase (including endo- and exo-β-glucanase) and β-glucosidase. These are all well known enzymes which participate in the hydrolysis of cellulose.

It is known to obtain sugar-containing liquor by the cellulase-hydrolysis of cellulose, said cellulase being obtained by fermentation of a microorganism of the genus Trichoderma. Various strains of *Trichoderma reesei* have been found to be particularly suitable for this purpose in view of the titre of cellulase obtained and the ratios of the three above-mentioned enzymes present in the accumulated cellulase, for example, *Trichoderma reesei* QM9414 (ATCC 26921). However, known processes of this type which use *Trichoderma reesei* strains are not always satisfactory, since the amount of accumulated cellulase may vary depending upon the cellulose-containing material used as the carbon source. If, for example, bagasses or rice straws, from which lignin has been removed, are used as the carbon source, a lower level of cellulase production is sometimes noted as compared to when the carbon source is Avicel or a cellulose powder containing a large amount of crystalline cellulose.

Whilst Avicel and cellulose powders are often used as carbon sources for the industrial preparation of cellulase by fermentation because they are good carbon sources, they have the disadvantage of being extremely expensive compared with other cellulose-containing raw materials. There is therefore a need to provide a more economical process for the preparation of cellulase using if possible cheaper waste materials, e.g. from agricultural and forest industries as the carbon source.

SUMMARY OF THE INVENTION

The present invention is based upon the discovery that a good yield of cellulase may be obtained using cheaper carbon sources by fermentation of certain mutant strain of the genus Trichoderma, which exhibit increased inducibility of cellulase by L-sorbose.

According to one aspect of the present invention, therefore, there is provided a process for the preparation of cellulase in which a microorganism of the genus Trichoderma, which is capable of producing cellulase, is cultured in order to accumulate cellulase in the culture medium and the resultant cellulase is harvested from the culture medium, characterized in that the said microorganism is a mutant strain of the genus Trichoderma, which exhhibit increased inducibility of cellulase by L-sorbose relative to that of a given parent strain.

Such mutant strains may be distinguished from the parent strain by the following test (hereinafter referred to as the 'clear zone' test). If small colonies of the organism grown on 0.3% (w/v) L-sorbose-containing agar plate medium are covered with 0.5% Walseth cellulose containing 50 mM acetic acid buffer solution (pH5.0) and incubated at 45° C. for 10–24 hours, a clear zone will be observed only around colonies of the mutant strains. This is due to the more immediate hydrolysis of the cellulose in the vicinity of the colonies of the mutant strains, as a result of the greater cellulase production by these colonies.

By the process of the present invention, a large amount of cellulase may be accumulated under the usual fermentation conditions which may be used with the known cellulase-producing microorganisms. It is thus possible by using this process to decrease the cost of cellulase for use in, for example, the production of fuel ethanol from cellulose.

Any strain of the genus Trichoderma which is capable of producing cellulase and which exhibits inducibility of cellulase by L-sorbose, detectable by the 'clear zone' test as hereinbefore described, may be used in the process. Preferred examples of such strains include *Trichoderma reesei* PC-1-4 (NRRL 15499), PC-3-7 (NRRL 15500), X-30 (NRRL 15501) and X-31 (NRRL 15502). These mutant strains have been deposited with the NRRL, U.S.A., under the provisions of the Budapest Treaty.

Mutant strains which exhibit increased inducibility of cellulase by L-sorbose may be derived from strains of the genus Trichoderma, capable of producing cellulase, by inducing mutations in conventional manner. Thus, suitable parent strains may be irradiated with ultraviolet rays or treated with known mutagens such as nitrosoguanidine. It is preferred to use *Trichoderma reesei* QM 9414 (ATCC 26921) as the parent strain.

*Trichoderma reesei* strains PC-1-4 (NRRL 15499), PC-3-7 (NRRL 15500), X-30 (NRRL 15501) and X-31 (NRRL 15502), which may be used in the process of the present invention, may be derived from *Trichoderma reesei* strain QM 9414 (ATCC 26921) as follows:

A potato-dextrose slant medium was used for culturing the strain at 25° C. for 7 days to form abundant spores. The spores were then suspended in a physiological saline solution at a concentration of about $1-3 \times 10^7$ per ml in order to treat them with N-methyl-N'-nitro-N-nitrosoguanidine (300 μg/ml; pH 7.0) at 30° C. for 30–120 minutes. The spores were collected from the suspension by centrifugation and well washed with a similar sodium chloride solution. The washed spores were diluted with a similar sodium chloride solution. The diluted spores were then smeared onto L-sorbose-containing agar plate medium, described hereinafter in Table 1, at a concentration of 100–300 spores per plate and cultured at 30° C. for 2 days. The resultant colonies were then covered with 0.5% Walseth cellulose containing 50 mM acetic acid buffer solution (pH5.0) and incubated further at 45° C. for 10–24 hours. Mutant strains were selected which gave rise to clear zones and which demonstrated lack of pigment formation when grown on potato-dextrose agar medium. Characteristics which may be used to distinguish the parent strain and the selected mutant strains are summarized in the following Table 1. The general mycological charateristics of *Trichoderma reesei* have been reported by E. G. Simmons in Abst. Intl. Mycol. Cong., Tampa, Fla., 1977, page 618.

TABLE 1

| | Strain | | | | |
|---|---|---|---|---|---|
| | QM9414 | PC-1-4 | PC-3-7 | X-30 | X-31 |
| (A) Characteristics on potato-dextrose agar medium | | | | | |
| Growth (colony size) | +++ | + | + | + | + |
| Spore forming ability | ++ | + | + | +++ | +++ |
| Pigment forming ability | + | − | − | − | − |
| (B) Size of clear-zone on L-sorbose agar plate medium** on carrying out the 'clear zone test' for cellulase inducibility by L-sorbose | − | ++++ | +++ | +++ | ++ |

**Composition of L-sorbose agar plate medium:-
L-sorbose [3 g], yeast extract [1 g], $(NH_4)_2SO_4$ [2 g], $KH_2PO_4$ [4 g], $Na_2HPO_4$ [6 g], $MgSO_4.7H_2O$ [200 mg], $FeSO_4.7H_2O$ [1 mg], $CaCl_2.2H_2O$[1 mg], Triton X-100 [commercial product of Rohm & Haas Co., U.S.A., 1 g], $H_3BO_3$ [10 μg], $MnSO_4.4H_2O$ [10 μg], $ZnSO_4.7H_2O$ [70 μg], $CuSO_4.5H_2O$ [50 μg], and $(NH_4)_6MO_7O_{24}.4H_2O$ [10 μg]. Made up to 1 liter with deionized water (pH 5.5).

The microorganisms which may be used for the purpose of the present invention may be cultured in conventional manner. Various organic and synthetic media which contain suitable sources of carbon and nitrogen may be used. Such media may, if desired, contain inorganic salts and other appropriate nutrients suitable for growth of the microorganism. Suitable carbon sources include, for example, filter papers, waste papers, bagasses, sweet sogrhams, rice plant hulls and straws, soybean wastes, woody wastes, stalks of corns and Nepia grass and various other cellulose-containing materials of plant origin. If desired, it is possible to use in combination with such carbon sources a suitable sugar source for example, sucrose, glucose, cane molasses, glycerol, or cellobiose in such an amount which does not affect the productivity of cellulase.

With regard to the sources of nitrogen, it is possible to use, for example, inorganic ammonium salts (e.g. ammonium sulfate) and organic ammonium salts (e.g. urea, amino acids, meat extract and peptone). With regard to inorganic salts, it is possible to use, for example, $KH_2PO_4$, $MgSO_4$, $CaCl_2$, $CuCl_2$, $FeSO_4$, $MnSO_4$ and $ZnSO_4$.

When the fermentation is effected at a temperature of from 20° to 32° C. and a pH of 3–6 with sufficient aeration for growth of the microorganism used, the activity of cellulase usually reaches a maximum 4–10 days after the beginning of the fermentation.

After completion of the culturing, the resultant liquor and/or enzyme preparation originating from the culture liquor may be used in conventional manner for hydroysis of cellulose.

Endo-$\beta$-glucanase, exo-$\beta$-glucanase and $\beta$-glucosidase in culture liquors and enzyme preparations originating from culture liquors may be assayed as follows:

Endo-$\beta$-glucanase may be assayed using carboxymethyl cellulose (sodium salt) as substrate. 10 g of carboxymethyl cellulose (sodium salt) was dissolved in 0.1M acetic acid buffer solution (1 l; pH 5). To 500 μl of this solution were added distilled water (450 μl) and a suitably diluted solution of a sample of enzyme (50 μl). The mixture was incubated at 45° C. for 30 minutes and reaction then stopped by placing the mixture in boiling water for 10 minutes. The amount of reduced sugar formed was determined by the method of Somogyi and Nelson. One unit of enzyme was defined as the amount which produces 1 μmol of the reduced sugar per minute.

Exo-$\beta$-glucanase may be assayed using Avicel SF (commercial product of Asahi Kasei Kogyo K.K., Japan). 0.15 g of Avicel SF was uniformly dispersed in 0.2M acetic acid buffer solution (4 ml; pH 5), to which was then added 1 ml of a sample solution of suitably diluted enzyme. Reaction was allowed to proceed at 45° C. for 60 minutes. The reaction solution was then treated in a similar manner to that described above.

$\beta$-glucosidase may be assayed using p-nitrophenyl-$\beta$-glucopyranoside, which was dissolved in 0.05M acetic acid buffer solution (pH 5) to obtain a 1 mM solution. To 1 ml of this solution was added a sample of suitably diluted enzyme (20 μl). Reaction was allowed to proceed at 45° C. for 10 minutes and then discontinued by addition of 1M sodium carbonate (2 ml) to the reaction solution. The amount of p-nitrophenol produced by the reaction was colormetrically determined by the OD value at 405 nm. One unit of enzyme was defined as the amount of which produces 1 μmol of p-nitrophenol per minute.

In the following Table 2, there is described a medium in which Trichoderma reesei may be cultured, as referred to in the following examples.

TABLE 2

Avicel [10 g], $KH_2PO_4$ [2 g], $(NH_4)_2SO_4$ [1.4 g], polypeptone [1 g], yeast extract [0.5 g], $MgSO_4.7H_2O$ [0.3 g], $CuCl_2.2H_2O$ [0.3 g], Tween 80 [1 g], solution of trace metals** [1 ml] and tartaric acid buffer solution [50 ml].

**Trace metal compounds contained in 100 ml:- $H_3BO_4$ [6 mg], $(NH_4)_6MO_7O_2.7H_2O$ [26 mg], $FeCl_2.6H_2O$ [100 mg], $CuSO_4.5H_2O$ [40 mg], $MnCl_2.4H_2O$ [8 mg] and $ZnCl_2$ [200 mg]. Made up to one liter with deionized water (pH 4.0).

The following non-limiting Examples illustrate the present invention.

EXAMPLE 1

5 different strains of Trichoderma reesei (QM 9414, PC-1-4, PC-3-7, X-30 and X-31) were respectively cultured at 25° C. for 7 days using potato-dextrose agar medium. One each occasion, the spores grown were transferred to a medium having the composition shown in Table 2, except that glucose (3 g) was used instead of Avicel pH 301 (commercial product of Asahi Kasei Kogyo K.K., Japan). Further culturing was carried out at 28° C. for 2 days with shaking. The cells were collected from the culture liquor and well-washed. They were then cultured at 28° C. for 21 hours with shaking to induce cellulase. The medium used (hereinafter referred to as Medium 3) had the following composition:

Washed cells (2–4 g), L-sorbose (1 g), MgSO$_4$.7H$_2$O (75 mg), CaCl$_2$.2H$_2$O (75 mg), Tween 80 (commercial product of Atlas Powders Co., U.S.A; 0.25 ml), solution of trace metals** (0.25 ml) and tartaric acid buffer solution (20 ml), made up to one liter with deionized water (pH 4).

**Trace metal compounds contained in 100 ml: H$_3$BO$_4$ (6 mg), (NH$_4$)$_6$MO$_7$O$_{24}$.4H$_2$O (26 mg), FeCl$_3$.6H$_2$O (100 mg), CuSO$_4$.5H$_2$O (40 mg), MnCl$_2$.4H$_2$O (8 mg) and ZnCl$_2$ (200 mg).

The results are shown in Table 3.

TABLE 3

| Production of Cellulase with L-sorbose as carbon source (Medium 3). | |
|---|---|
| Strain | Units of endo-$\beta$-glucanase/ mg (cells) |
| QM 9414 | 0.06 |
| PC-1-4 | 1.3 |
| PC-3-7 | 1.8 |
| X-30 | 1.3 |
| X-31 | 1.6 |

(A similar pattern of inducibility by L-sorbose was obtained on assaying exo-$\beta$-glucanase or $\beta$-glucosidase).

Identical tests were carried out using two further media, one having the same compostion as Medium 3 except that sorbose was absent, and the other having the same composition as Medium 3 except that sorbose was replaced by glucose. No cellulose production was observed in either case. Table 3 clearly indicates that inducibility of cellulase by L-sorbose in the 4 mutant strains of *Trichoderma reesei* PC-1-4, PC-3-7, X-30 and X-31 is more than 20-fold greater than in the parent strain, QM 9414.

EXAMPLE 2

Spores of each of the strains QM 9414, PC-1-4, PC-3-7, X-30 and X-31 were prepared in a similar manner to that described in Example 1 and transferred both to a medium having the composition shown in Table 2, and medium having the same compostiton except that Avicel was replaced by 1% bagasse (50 ml of each medium in a 300 ml Erlenmeyer flask).

Lignin was removed from the bagasse prior to addition to the second medium by treatment with alkali. The results obtained for endo-$\beta$-glucanase production are shown in Table 4.

TABLE 4

| Strain | Avicel | Bagasse |
|---|---|---|
| | (units endo-$\beta$-glucanase/ml) | |
| QM 9414 | 21 | 8 |
| PC-1-4 | 25 | 21 |
| PC-3-7 | 26 | 23 |
| X-30 | 22 | 22 |
| X-31 | 24 | 25 |

From this table, it is apparent that when bagasse was used as the carbon source, the 4 mutant strains produced 2.6–3.1 fold higher endo-$\beta$-glucanase than the parent strain, QM 9414. While endo-$\beta$-glucanase production by strain QM 9414 in the presence of Avicel as carbon source was about 2.5 times the production by this strain in the presence of bagasse, endo-$\beta$-glucanase production by the mutant strains was either substantially similar or identical in the presence of the two carbon sources. Similar productivity ratios were obtained for exo-$\beta$-glucanase (results not given).

EXAMPLE 3

Avicel in the medium as shown in Table 2 was replaced by 1% rice straw, from which lignin had been removed by treatment with alkali. The medium was used for culturing spores of each of the strains QM 9414, PC-3-7, and X-31, which had been prepared by the method of Example 1. By culturing in a manner similar to that described in Example 2, the results shown in Table 5 were obtained.

TABLE 5

| Strain | endo-$\beta$-glucanase (units/ml) |
|---|---|
| QM 9414 | 9 |
| PC-3-7 | 20 |
| X-30 | 21 |

From this table, it is apparent that, as in Example 2 when identical final culture medium was used except that bagasse was used as the carbon source, the strains PC-3-7 and X-31 produced more than twice the number of units of endo-$\beta$-glucanase than strain QM 9414.

EXAMPLE 4

Spores of each of the strains QM 9414 and PC-3-7, prepared in a manner similar to that described in Example 1, were cultured in a manner similar to that described in Example 2, using a culture medium have the composition shown in Table 2 except that 1% Avicel was replaced by 3% bagasse, 0.14% ammonium sulfate was replaced by 0.42% ammonium sulfate and 100 ml of 50 mM tartaric acid buffer solution was used. The results for endo-$\beta$-glucanase production are shown in Table 6.

TABLE 6

| Strain | endo-$\beta$-glucanase (units/ml) |
|---|---|
| QM 9414 | 16 |
| PC-3-7 | 50 |

This table indicates that by the use of bagasse at a higher concentration than in Example 2, a more than 3-fold greater amount of cellulase was obtained in the case of strain PC-3-7 than in the case of strain QM 9414.

We claim:

1. A process for the preparation of cellulase in which a microorganism of the genus Trichoderma, which is capable of producing cellulase, is cultured in order to accumulate cellulase in the culture medium and the resultant cellulase is harvested from the culture medium, characterised in that the said microorganism is a mutant strain of the genus Trichoderma, which exhibits increased inducibility of cellulase by L-sorbose relative to that of a given parent strain.

2. The process of claim 1, wherein said mutant strain is of the species *Trichoderma reesei*.

3. The process of claim 1, wherein said mutant strain is selected from *Trichoderma reesei* PC-1-4 (NRRL 15449), *Trichoderma reesei* PC-3-7 (NRRL 15500), *Trichoderma reesei* X-30 (NRRL 15501) and *Trichoderma reesei* X-31 (NRRL 15502).

4. The process of claim 1, wherein the carbon source of said medium comprises at least one member selected from filter papers, waste papers, bagasses, wheat straws, sweet sorghams, rice plant hulls and straws, soybean wastes, woody wastes and stalks of corns and Nepia grass.

5. The process of claim 1, wherein said medium contains a sugar source which comprises at least one member selected from sucrose, glucose, cane molasses, glycerol and cellobiose.

6. The process of claim 1, wherein culturing is effected at a temperature of from 20° to 32° C. and a pH of from 3 to 6 for 4 to 10 days under aerobic conditions.

7. A biologically pure culture of a mutant strain of *Trichoderma reesei* selected from PC-1-4 (NRRL 15449), PC-3-7 (NNRL 15500), X-30 (NRRL 15501), X-31 (NRRL 15502) and mutants thereof which exhibit inducibility of cellulase by L-sorbose.

* * * * *